United States Patent [19]
Whitton et al.

[11] Patent Number: 6,153,750
[45] Date of Patent: Nov. 28, 2000

[54] PROCESS FOR PREPARAING (E)-METHYL 2-[2-(6-(2-CYANOPHENOXY)-PYRIMIDIN-4-YLOXY)PHENYL]-3-METHOXYPROPENOATE IN THE ABSENCE OF COPPER(SALT) AND OF N,N-DIMETHYLFORMAMIDE

[75] Inventors: Alan John Whitton, Falkirk; Ian George Fleming; Robert Comgall Ewins, both of Grangemouth; Raymond Vincent Heavon Jones, West Lothian; Samuel McNeish, Grangemouth, all of United Kingdom

[73] Assignee: ZENECA Limited, United Kingdom

[21] Appl. No.: 09/297,169

[22] PCT Filed: Oct. 28, 1997

[86] PCT No.: PCT/GB97/02793

§ 371 Date: Jun. 10, 1999

§ 102(e) Date: Jun. 10, 1999

[87] PCT Pub. No.: WO98/18767

PCT Pub. Date: May 7, 1998

[30] Foreign Application Priority Data

Oct. 28, 1996 [GB] United Kingdom .................. 96223458

[51] Int. Cl.$^7$ .................................................. C07D 239/52
[52] U.S. Cl. .................................................. 544/312
[58] Field of Search ............................... 544/312

[56] References Cited

FOREIGN PATENT DOCUMENTS

| 0 382 375 | 8/1990 | European Pat. Off. . |
| 2 291 874 | 2/1996 | United Kingdom . |
| 98/07707 | 2/1998 | WIPO . |

*Primary Examiner*—John M. Ford
*Attorney, Agent, or Firm*—Thomas R. Savitsky

[57] ABSTRACT

A process for preparing (E)-methyl 2-[2-(6-(-cyanophenoxy)pyrimidin-4-yloxy)phenyl]-3-methoxypropenoate comprising contacting (E)-methyl 2-[2-(6-chloropyrimidin-4-yloxy)phenyl]-3-methoxypropenoate or methyl 2-[2-(6-chloropyrimidin-4-yloxy)phenyl]-3,3-dimethoxypropanoate with 2-cyanophenate anions, the process being conducted in the absence of copper or a copper salt and in the absence of N,N-dimethylformamide. The 2-cyanophenate anions are generated in situ by reacting 2-cyanophenol with an alkali metal carbonate.

7 Claims, No Drawings

PROCESS FOR PREPARAING (E)-METHYL 2-[2-(6-(2-CYANOPHENOXY)-PYRIMIDIN-4-YLOXY)PHENYL]-3-METHOXYPROPENOATE IN THE ABSENCE OF COPPER(SALT) AND OF N,N-DIMETHYLFORMAMIDE

The present invention relates to a process for the preparation of (E)-methyl 2-[2-(6-(2-cyanophenoxy)pyrimidin-4-yloxy)phenyl]-3-methoxypropenoate, a plant fungicide.

Methods of preparing (E)-methyl 2-[2-(6-(2-cyanophenoxy)pyrimidin-4-yloxy)phenyl]-3-methoxypropenoate, and intermediates therefor, are described in EP-A2-0382375, WO 92/08703, GB2291874 and PCT Application No. PCT/GB97/02015. The method for preparing (E)-methyl 2-[2-(6-(2-cyanophenoxy)pyrimidin-4-yloxy)phenyl]-3-methoxypropenoate described in WO 92/08703 involves heating a mixture of (E)-methyl 2-[2-(6-chloropyrimidin-4-yloxy)phenyl]-3-methoxypropenoate, 2-cyanophenol, potassium carbonate and cuprous chloride in N,N-dimethylformamide at 120° C. for 90 minutes. The method described in PCT/GB97/02015 involves heating methyl 2-[2-(6-chloropyrimidin-4-yloxy)phenyl]-3,3-dimethoxypropanoate with 2-cyanophenol at 90–95° C. to form (E)-methyl 2-[2-(6-chloropyrimidin-4-yloxy)phenyl]-3-methoxypropenoate which is then heated to 120–125° C. in N,N-dimethylformamide with potassium carbonate to form the desired product.

The present invention provides a process for preparing (E)-methyl 2-[2-(6-(2-cyanophenoxy)pyrimidin-4-yloxy)phenyl]-3-methoxypropenoate comprising contacting (E)-methyl 2-[2-(6-chloropyrimidin-4-yloxy)phenyl]-3-methoxypropenoate or methyl 2-[2-(6-chloropyrimidin-4-yloxy)phenyl]-3,3-dimethoxypropanoate with 2-cyanophenate anions, the process being conducted in the absence of copper or a copper salt and in the absence of N,N-dimethylformamide.

The process of the invention may be conducted in the complete absence of any solvent or mixture of solvents, miscible or immiscible, including water itself. In this case the reaction mixture will be in the form of a melt.

Alternatively, the process may be conducted using water as the only solvent. In this case the water may be generated in situ or may be specifically added, or both. Water is generated in situ when an appropriate base is used to generate 2-cyanophenate anions in situ with 2-cyanophenol, as will be the usual procedure. Such a base will be, for example, a hydroxide, carbonate or bicarbonate. Bases which can be used which do not generate water in situ include phosphates and tertiary amines.

The process may also be conducted in the presence of a water-immiscible solvent or a mixture of water-immiscible solvents in the complete absence of water, with water generated only in situ or with added water and/or water generated in situ. Where water is present with a water-immiscible solvent or mixture of water-immiscible solvents, the process will take place in a two phase liquid system. Preferred water-immiscible solvents include cyclic hydrocarbons, such as aromatic hydrocarbons, for example toluene and xylenes, and alicyclic hydrocarbons, for example methylcyclohexane.

The process may also be conducted in the presence of other solvents which may be miscible, immiscible or partially miscible with water, including alcohols such as 2-propanol, 1-butanol, 2-pentanol and cyclohexanol, ketones such as methyl ethyl ketone, methyl iso-butyl ketone and 2,4-dimethyl-3-pentanone, ethers such as tert-butyl methyl ether, glymes such as 2-methoxyethyl ether, ethylene glycol dimethyl ether, ethylene glycol diethyl ether and esters such as ethyl acetate and iso-butyl acetate.

Thus the process of the invention includes the use of any suitable solvent other than N,N-dimethylformamide.

2-Cyanophenate anions can be used directly in the process of the present invention, for example by using an alkali metal 2-cyanophenate (such as sodium or potassium 2-cyanophenate). Alternatively, 2-cyanophenate anions can be prepared in situ by reacting 2-cyanophenol with a suitable base, which may be a suitable hydroxide such as an alkali metal hydroxide, for example sodium or potassium hydroxide, a suitable carbonate such as an alkali metal carbonate, for example sodium or potassium carbonate, a suitable bicarbonate such as an alkali metal bicarbonate, for example sodium or potassium bicarbonate, a suitable phosphate such as an alkali metal phosphate, mono-, di- or tribasic, of the formula $MH_2PO_4$, $M_2HPO_4$ or $M_3PO_4$ (where M is an alkali metal, e.g. sodium or potassium), or a suitable tertiary amine of formula $R^1R^2R^3N$ wherein $R^1$, $R^2$ and $R^3$ are, independently, $C_{1-10}$ alkyl (especially $C_{1-6}$ alkyl), $C_{3-6}$ cycloalkyl, aryl (especially phenyl, but also pyridyl) or aryl($C_{1-4}$) alkyl (especially benzyl), or two or three of $R^1$, $R^2$ and $R^3$ join together with the nitrogen atom to which they are attached to form one, two or three, 5-, 6- or 7-membered alicyclic rings optionally fused and optionally containing a second ring nitrogen atom.

Alkyl groups are straight or branched chain and, unless stated otherwise, contain from 1 to 10, especially from 1 to 6, particularly from 1 to 4, carbon atoms. Examples are methyl, ethyl, iso-propyl, n-propyl, n-butyl, sec-butyl, iso-butyl and tert-butyl.

Cycloalkyl groups comprise 3 to 6 carbon atoms and are optionally substituted by $C_{1-6}$ alkyl. Examples are cyclohexyl, 2-methylcyclohexyl and 2-ethylcyclohexyl.

Tertiary amines of formula $R^1R^2R^3N$ are, for example, N,N-diisopropylethylamine, N,N-dimethylaniline, triethylamine, N,N-diisopropylmethylamine, N,N-diisopropylisobutylamine, N,N-diisopropyl-2-ethylbutylamine, N,N-dicyclohexylmethylamine, N,N-dicyclohexylethylamine, 1,5-diazabicyclo[4.3.0]non-5-ene, 1,4-diazabicyclo[2.2.2]octane or 2- or 4-dimethylaminopyridine.

It is preferred that the process is conducted at a temperature in the range of 10–250° C., usually at an elevated temperature in the range of 50–250° C., especially in the range of 90–190° C., and particularly in the range of 90–130° C., typically in the range of 100–130° C.

It is also preferred that the process of the present invention is conducted at atmospheric pressure or under a positive pressure.

Usually the process will be conducted by heating the reactant to an elevated temperature. However, the process can be carried out at ambient temperature, with or without a solvent, by conducting it in a ball mill.

If the 2-cyanophenate anions are prepared in situ by reaction of 2-cyanophenol with a suitable phosphate, such as sodium or potassium phosphate, when the process is terminated, the phosphorus residues remaining may be recycled to phosphate by means known in the art. The regenerated phosphate can then be used again.

When the process is carried out in a two-phase system, particularly when water and a water-immiscible solvent are present, it may be advantageous to include a phase transfer catalyst. By the term "phase transfer catalyst" is meant a substance which, being at least partly present in or wetted by a first (usually organic) phase, promotes reaction between a reactant in the first phase and a reactant which it transfers to the first phase from a second (usually aqueous but sometimes solid) phase. After reaction, the phase transfer catalyst is released for transferring further reactant. Phase transfer catalysts are reviewed by E. V. Dehmlow in *Angewante Chemie* (International Edition), 13 (3), 170 (1974). Other reviews are by Jozef Dockx in *Synthesis* (1973), 441–456 and by C. M. Starks in *JACS.*, (93) 1, Jan. 13, 1971, 195–199.

Suitably the phase transfer catalyst is a quaternary ammonium or phosphonium salt preferably containing bulky organic groups, usually alkyl or aralkyl groups, to make it soluble in the organic phase. It is preferred that the phase catalyst is a tetraalkyl or aralkyl (eg benzyl) trialkyl ammonium or phosphonium salt in which the total number of carbon atoms attached to each nitrogen or phosphorus atom is greater than 10. There is little advantage in the number being above 70. It is especially preferred that the number should be in the range of from 16 to 40.

Examples of quaternary ammonium salts are: cetyltrimethylammonium bromide, dicetyldimethylammonium chloride, octyltributylammonium bromide, trioctylmethylammonium chloride (available as Aliquat™ 336), benzyldimethyllaurylammonium chloride, benzyltriethylammonium chloride, dilauryldimethylammonium chloride, tetrabutylammonium bromide and dieicosyldimethylammonium chloride. Examples of quaternary phosphonium salts are cetyltripropylphosphonium bromide and triphenylethylphosphonium bromide. Other phase transfer catalysts which may be suitable include crown ethers, polyethylene glycol variants and N-methyl-2-pyrrolidinone.

When the process is carried out in the presence of added water, the amount of water added may be up to 52 molar equivalents of propenoate or propanoate starting material, for example, in the range of 5 to 30 molar equivalents, typically about 11 molar equivalents.

The following Examples illustrate the invention.

EXAMPLE 1

To a solution of potassium hydroxide (12.0 g) in water (10 g) was added, with stirring, 2-cyanophenol (13.2 g). The resulting solution was added, over 5 minutes, to (E)-methyl 2-[2-(6-chloropyrimidin-4-yloxy)phenyl]-3-methoxypropenoate (32.8 g) at 95° C. and the temperature was maintained at 95–100° C. during the addition. Tetrabutylammonium bromide (1.5 g) was then added and the resulting mixture stirred for 20 hours at 95–100° C. The reaction mixture was mixed with water and toluene and the organic layer separated. The toluene solution contained (E)-methyl 2-[2-(6-(2-cyanophenoxy)pyrimidin-4-yloxy)phenyl]-3-methoxypropenoate (72.6% yield).

EXAMPLE 2

A solution of the potassium salt of 2-cyanophenol was prepared by mixing 2-cyanophenol (13.2 g) and potassium carbonate (8.4 g) in water (30 g). This solution was added to (E)-methyl 2-[2-(6-chloropyrimidin-4-yloxy)phenyl]-3-methoxypropenoate (32.8 g) over 5 minutes while maintaining the temperature at 95–100° C. The resulting mixture was stirred at 110° C. for 5 hours. The reaction mixture was mixed with water and toluene and the organic layer separated. The toluene solution contained (E)-methyl 2-[2-(6-(2-cyanophenoxy)pyrimidin-4-yloxy)phenyl]-3-methoxypropenoate (70.8% yield).

EXAMPLE 3

A solution of the potassium salt of 2-cyanophenol was prepared by mixing 2-cyanophenol (13.2 g) and potassium carbonate (9.6 g) in water (30 g). This solution was added to (E)-methyl 2-[2-(6-chloropyrimidin-4-yloxy)phenyl]-3-methoxypropenoate (32.8 g) over 5 minutes while maintaining the temperature at 95–100° C. The resulting mixture was stirred at 120° C. for 4 hours. The reaction mixture was mixed with water and toluene and the organic layer separated. The toluene solution contained (E)-methyl 2-[2-(6-(2-cyanophenoxy)pyrimidin-4-yloxy)phenyl]-3-methoxypropenoate (75.6% yield).

EXAMPLE 4

A solution of the potassium salt of 2-cyanophenol was prepared by mixing 2-cyanophenol (13.2 g) and potassium hydroxide (6.8 g) in water (7 g). This solution was added to (E)-methyl 2-[2-(6-chloropyrimidin-4-yloxy)phenyl]-3-methoxypropenoate (32.8 g) over 5 minutes while maintaining the temperature at 95–100° C. The resulting mixture was stirred at 120–20 C. for 2 hours. The reaction mixture was mixed with water and toluene and the organic layer separated. The toluene solution contained (E)-methyl 2-[2-(6-(2-cyanophenoxy)pyrimidin-4-yloxy)phenyl]-3-methoxypropenoate (61.5% yield).

EXAMPLE 5

A slurry of the potassium salt of 2-cyanophenol containing potassium chloride was prepared by mixing 2-cyanophenol (13.2 g), potassium hydroxide (6.8 g) and potassium chloride (20 g) in water (10 g). This solution was added to (E)-methyl 2-[2-(6-chloropyrimidin-4-yloxy)phenyl]-3-methoxypropenoate (32.8 g) over 5 minutes while maintaining the temperature at 95–100° C. The resulting mixture was stirred at 110° C. for 3 hours. The reaction mixture was mixed with water and toluene and the organic layer separated. The toluene solution contained (E)-methyl 2-[2-(6- (2-cyanophenoxy)pyrimidin-4-yloxy)phenyl]-3-methoxypropenoate (77.7% yield).

EXAMPLE 6

A mixture of 2-cyanophenol (12.6 g), potassium carbonate (8.28 g) and (E)-methyl 2-[2-(6-chloropyrimidin4-yloxy)phenyl]-3-methoxypropenoate (33.0 g) was heated at 120° C. for 3 hours. The mixture was then cooled to 100° C. after which methanol (40 ml) was added to help cooling to 65° C. The resulting mixture was cooled to 0–5° C. and kept at this temperature for 1 hour. The mixture was filtered to leave (E)-methyl 2-[2-(6-(2-cyanophenoxy)pyrimidin-4-yloxy)phenyl]-3-methoxypropenoate as the residue (87.5%

The following Examples were carried out using the methodology of Example 6, 2-cyanophenol (12.6 g), (E)-methyl 2-[2-(6-chloropyrimidin-4-yloxy)phenyl]-3-methoxypropenoate (Compound A, 33.0 g, 0.1 mol) and potassium carbonate, sodium carbonate or N,N-diisopropylethylamine as a base.

| Example No. | Base | Molar ratio of Base to Compound A | Time (minutes) | Temperature (° C.) | Yield (Area %) |
| --- | --- | --- | --- | --- | --- |
| 7 | $K_2CO_3$ | 0.45 | 240 | 120 | 63.6 |
| 8 | $K_2CO_3$ | 0.45 | 300 | 120 | 79.1 |
| 9 | $K_2CO_3$ | 0.6 | 150 | 120 | 96.3 |
| 10 | $K_2CO_3$ | 0.6 | 60 | 120 | 84.0 |
| 11 | $K_2CO_3$ | 0.6 | 180 | 120 | 96.6 |

-continued

| Example No. | Base | Molar ratio of Base to Compound A | Time (minutes) | Temperature (° C.) | Yield (Area %) |
|---|---|---|---|---|---|
| 12 | [(CH$_3$)$_2$CH]$_2$NC$_2$H$_5$ | 1.5 | 90 | 120 | 36.0 |
| 13 | Na$_2$CO$_3$ | 0.6 | 60 | 120 | 14.4 |

The following Examples were carried out using the methodology of Example 6 except that a solvent was also used.

| Example No. | Base | Molar ratio of Base to Compound A | Solvent | Time (minutes) | Temperature (° C.) | Yield (Area %) |
|---|---|---|---|---|---|---|
| 14 | K$_2$CO$_3$ | 0.6 | toluene (30 ml) | 300 | 100 | 40.4 |
| 15 | KOH | 0.6 | toluene (20 ml) | 150 | 100 | 41.4 |
| 16 | KOH | 1.2 | toluene (20 ml) | 220 | 120 | 89.0 |
| 17 | [(CH$_3$)$_2$CH]$_2$NC$_2$H$_5$ | 1.5 | xylene (65 ml) | 240 | 120 | 54.5 |
| 18 | KOH | 1.1 | 2-MEE (30 ml) | 248 | 120 | 86.6 |
| 19 | KOH | 1.1 | 2-MEE (30 ml) | 80 | 150 | 89.0 |
| 20 | K$_2$CO$_3$ | 0.75 | 2-MEE (30 ml) | 240 | 120 | 89.0 |

EXAMPLE 21

To a solution of potassium hydroxide (11.6 g) in water (15 ml) was added, with stirring, 2-cyanophenol (12.7 g). The resulting solution was added dropwise to (E)-methyl 2-[2-(6-chloropyrimidin-4-yloxy)phenyl]-3-methoxypropenoate (38.8 g) at 100° C. and the temperature was maintained at 95–100° C. during the addition. The system was set-up with a Dean and Stark head. The reaction mixture was heated at 120° C. for 25 minutes, cooled to 80° C., a mixture of water (50 ml) and toluene (30 ml) added and the resulting mixture allowed to stand for 18 hours. The resulting mixture was heated to 80° C., left for 30 minutes, transferred to a separator, left for 30 minutes and the organic layer, containing (E)-methyl 2-[2-(6-(2-cyanophenoxy)pyrimidin-4-yloxy)phenyl]-3-methoxypropenoate, was separated (58.5% yield).

EXAMPLE 22

A mixture of 2-cyanophenol (41.0 g), potassium carbonate (62.1 g), potassium fluoride (12.3 g), tetrabutylammonium bromide (17.1 g), (E)-methyl 2-[2-(6-chloropyrimidin-4-yloxy)phenyl]-3-methoxypropenoate (98.9 g) and water (210 g) was heated at 90–95° C. for 22 hours. The reaction mixture was mixed with toluene and a further quantity of water. The organic layer was then separated. Toluene was removed from the organic phase by vacuum distillation (100° C., 20 mmHg). The melt was cooled to 85° C. after which methanol (120 ml) was added to help cooling to 70° C. The resulting mixture was cooled to 40° C. and kept at this temperature for 1 hour. It was then further cooled to 0–5° C. and held for another 1 hour period. The mixture was filtered to leave (E)-methyl 2-[2-(6-(2-cyanophenoxy)pyrimidin-4-yloxy)pheny]-3-methoxypropenoate as the residue (85.5% isolated yield).

EXAMPLE 23

(E)-methyl 2-[2-(6-chloropyrimidin-4-yloxy)phenyl]-3-methoxypropenoate in N,N-dimethylformamide (256.8 g, 33.69% strength) was vacuum distilled to remove the solvent. A solution of the potassium salt of 2-cyanophenol was then prepared by mixing 2-cyanophenol (37.0 g) and potassium carbonate (56.7 g) in water (209 g). This solution was added to the (E)-methyl 2-[2-(6-chloropyrimidin-4-yloxy) phenyl]-3-methoxypropenoate melt, which had previously been cooled to 80° C. Potassium fluoride (11.1 g) and tetrabutylammonium bromide (16.1 g) was then added to the reaction solution. The resulting mixture was stirred at 100° C. for 23 hours. Any distillates were allowed to come off under atmospheric conditions. Toluene and a further quantity of water was added to the solution. The organic layer was then separated. Toluene was removed from the organic phase by vacuum distillation (100° C., 20 mmHg). The melt was cooled to 90° C. after which methanol (108 ml) was added to help cooling to 65–75° C. The resulting mixture was cooled to 40° C. and kept at this temperature for 2 hours. It was then further cooled to 0–5° C. and held for another 1 hour period. The mixture was filtered to leave (E)-methyl 2-[2-(6-(2-cyanophenoxy)pyrimidin-4-yloxy)phenyl]-3-methoxypropenoate as the residue (67.0% isolated yield).

EXAMPLE 24

A mixture of 2-cyanophenol (13.2 g), potassium carbonate (20.7 g), polyethylene glycol 400 (20.0 g), (E)-methyl 2-[2-(6-chloropyrimidin-4-yloxy)phenyl]-3-methoxypropenoate (32.8 g) and water (77 g) was heated at 96° C. for 16 hours. The temperature of the solution was then raised to 105° C. and held for a further 12 hours. Any distillates were allowed to come off under atmospheric conditions. (E)-methyl 2-[2-(6-(2-cyanophenoxy)pyrimidin-4-yloxy)phenyl]-3-methoxypropenoate was produced (86.6 area %).

EXAMPLE 25

A mixture of 2-cyanophenol (39.7 g), potassium carbonate (62.2 g), polyethylene glycol 400 (60.0 g), (E)-methyl 2-[2-(6-chloropyrimidin-4-yloxy)phenyl]-3-methoxypropenoate (98.3 g) and toluene (130 g) was heated at 105° C. for 16 hours. (E)-methyl 2-[2-(6-(2-cyanophenoxy)pyrimidin-4-yloxy)phenyl]-3-methoxypropenoate was produced (89.5 area %).

EXAMPLE 26

A mixture of 2-cyanophenol (13.2 g), potassium carbonate (20.7 g), N-methyl-2-pyrrolidinone (15.0 g), (E)-methyl 2-[2-(6-chloropyrimidin-4-yloxy)phenyl]-3-methoxypropenoate (32.8 g) and water (35 g) was heated at 105° C. for 15 hours. Any distillates were allowed to come off under atmospheric conditions. The reaction mixture was mixed with toluene. The organic layer was then separated.

Toluene and N-methyl-2-pyrrolidinone were removed from the organic phase by vacuum distillation (110° C., 20 mmHg). The melt was cooled to 90° C. after which methanol (40 ml) was added to help cooling to 65–75° C. The resulting mixture was cooled to ambient and kept at this temperature overnight. It was then further cooled to 0–5° C. and held for another 1 hour period. The mixture was filtered to leave (E)-methyl 2-[2-(6-(2-cyanophenoxy)pyrimidin-4-yloxy) phenyl]-3-methoxypropenoate as the residue (68.2% isolated yield).

EXAMPLE 27

Methyl 2-[2-(6-chloropyrimidin-4-yloxy)phenyl]-3,3-dimethoxypropanoate in methylcyclohexane/chloromethoxypyrimidine (200.9 g, 59.91% strength) was vacuum distilled to leave the propanoate melt. A solution of the potassium salt of 2-cyanophenol was then prepared by mixing 2-cyanophenol (53.2 g) and potassium carbonate (81.2 g) in water (275 g). This solution was added to the methyl 2-[2-(6-chloropyrimidin-4-yloxy)phenyl]-3,3-dimethoxypropanoate melt, which had previously been cooled to 90° C. Potassium fluoride (15.9 g) and tetrabutylammonium bromide (21.5 g) was then added to the reaction solution. The resulting mixture was stirred at 105° C. for 23 hours. Any distillates were allowed to come off under atmospheric conditions. (E)-methyl 2-[2-(6-(2-cyanophenoxy)pyrimidin-4-yloxy)phenyl]-3-methoxypropenoate was produced (77.9 area %).

EXAMPLE 28

Methyl 2-[2-(6-chloropyrimidin-4-yloxy)phenyl]-3,3-dimethoxypropanoate in methylcyclohexane/chloromethoxypyrimidine (178.6 g, 59.91% strength) was vacuum distilled to leave the propanoate melt. A solution of the potassium salt of 2-cyanophenol was then prepared by mixing 2-cyanophenol (64.6 g) and potassium carbonate (72.3 g) in water (245 g). This solution was added to the methyl 2-[2-(6-chloropyrimidin-4-yloxy)phenyl]-3,3-dimethoxypropanoate melt, which had previously been cooled to 90° C. Potassium fluoride (14.2 g) and tetrabutylammonium bromide (19.1 g) was then added to the reaction solution. The resulting mixture was stirred at 105° C. for 16 hours under atmospheric distillation. (E)-methyl 2-[2-(6-cyanophenoxy)pyrimidin-4-yloxy)phenyl]-3-methoxypropenoate was produced (61.3 area %). Further quantities of potassium fluoride (7.1 g), tetrabutylammonium bromide (9.1 g) and potassium carbonate (36.0 g) was added to the reaction solution. The solution was then allowed to distill under atmospheric pressure at 105–120° C. over a period of ca. 5 hours. Toluene and a further quantity of water was added to the solution. The organic layer was then separated. Toluene was removed from the organic phase (100° C., 20 mmHg). The melt was cooled to 85–90° C. after which methanol
(140 ml) was added to help cooling to 60–65° C. The resulting mixture was cooled to ambient and held overnight. It was then cooled to 0–5° C. and kept at this temperature for 1 hour. The mixture was filtered to leave (E)-methyl 2-[2-(6-(2-cyanophenoxy)pyrimidin4-yloxy)phenyl]-3-methoxypropenoate as the residue (53.2% isolated yield).

EXAMPLE 29

Methyl 2-[2-(6-chloropyrimidin-4-yloxy)phenyl]-3,3-dimethoxypropanoate in methylcyclohexane/chloromethoxypyrimidine (184.1 g, 59.91% strength) was vacuum distilled to leave the propanoate melt. A solution of the potassium salt of 2-cyanophenol was then prepared by mixing 2-cyanophenol (45.2 g) and potassium carbonate (98.1 g) in water (50 g). This solution was added to the melt, which had previously been cooled to 70° C. Potassium fluoride (14.5 g) and tetrabutylammonium bromide (19.3 g) was then added to the reaction solution. The reaction solution was then heated to 120° C. and held for 3 hours. Distillates were removed under atmospheric conditions. (E)-methyl 2-[2-(6-(2-cyanophenoxy)-pyrimidin-4-yloxy) phenyl]-3-methoxypropenoate was produced (86.0 area %).

EXAMPLE 30

Methyl 2-[2-(6-chloropyrimidin-4-yloxy)phenyl]-3,3-dimethyoxypropanoate in methylcyclohexane/chloromethoxypyrimidine (170.5 g, 59.91% strength) was vacuum distilled to leave the propanoate melt. A solution of the potassium salt of 2-cyanophenol was then prepared by mixing 2-cyanophenol (44.4 g) and potassium carbonate (45.6 g) in water (66 g). This solution was added to the melt which had previously been cooled to 90° C. The reaction solution was heated to 120° C. and held for 3 hours. Any distillates were allowed to come off under atmospheric conditions. (E)-methyl 2-[2-(6-(2-cyanophenoxy)pyrimidin-4-yloxy)-phenyl]-3-methoxypropenoate was produced (84.2 area %). Toluene and a further quantity of water were added to the solution. The organic layer was then separated. Toluene was removed from the organic phase (100° C., 20 mmHg). The melt was cooled to 90 ° C. after which methanol (132 ml) was added to help cooling to 60–70° C. The resulting mixture was cooled to ambient and held over the weekend. It was then cooled to 0–5° C. and kept at this temperature for 1 hour. The mixture was filtered to leave (E)-methyl 2-[2-(6-(2-cyanophenoxy)pyrimidin-4-yloxy) phenyl]-3-methoxypropenoate as the residue (46.3% isolated yield).

EXAMPLE 31

Methyl 2-[2-(6-chloropyrimidin-4-yloxy)phenyl]-3,3-dimethoxypropanoate in methylcyclohexane/chloromethoxypyrimidine (185.5 g, 59.71% strength) was vacuum distilled to leave the propanoate melt. A solution of the potassium salt of 2-cyanophenol was then prepared by mixing 2-cyanophenol (49.0 g) and potassium carbonate (30.4 g) in water (50 g). This solution was added to the methyl 2-[2-(6-chloropyrimidin-4-yloxy)phenyl]-3,3-dimethoxypropanoate melt, which had previously been cooled to 70° C. The reaction solution was then heated to 120° C. and held for 2 hours. Any distillates were allowed to come off under atmospheric conditions. (E)-methyl 2-[2-(6-(2-cyanophenoxy)pyrimidin-4-yloxy)phenyl]-3-methoxypropenoate was produced (39.4 area %). The reaction solution was then distilled under vacuum (20 mmHg) at 95° C. for 2 hours and at 120° C. for 1 hour. No further demethanolysis was evident. The reagents were cooled to 95° C. before an additional amount of potassium carbonate (45.6 g) was charged. The solution was again distilled under vacuum (20 mmHg) at 95° C. for 20 minutes and at 120° C. for 20 mins. (E)-Methyl 2-[2-(6-(2-cyanophenoxy) pyrimidin-4-yloxy)phenyl]-3-methoxypropenoate was produced (55.6 area %).

EXAMPLE 32

Methyl 2-[2-(6-chloropyrimidin-4-yloxy)phenyl]-3,3-dimethoxypropanoate in methylcyclohexane/chloromethoxypyrimidine (181.5 g, 60.57 % strength) was vacuum distilled to leave the propanoate melt. A solution of the potassium salt of 2-cyanophenol was then prepared by mixing 2-cyanophenol (46.8 g), potassium carbonate (71.5 g) and polyethylene glycol 400 (7.0 g) in water (50 g). The solution was then added to the melt, which had previously been cooled to 70° C. The reaction solution was then held at 105° C. for 17 hours under atmospheric distillation. 53.1 Area % of (E)-methyl 2-[2-(6-(2-cyanophenoxy)pyrimidin-4-yloxy)phenyl]-3-methoxypropenoate was produced. The reaction mixture was held for a further 4.5 hours at 120° C. under atmospheric distillation. Toluene and a further quantity of water was added to the solution. The organic layer was then separated. Toluene was removed from the organic phase (100° C., 20 mmHg). The melt was cooled to 90° C. after which methanol (140 ml) was added. The resulting mixture was cooled to ambient and held overnight. It was then cooled to 0–5° C. and held at this temperature for 1 hour. The mixture was filtered to leave (E)-methyl 2-[2-(6-(2-cyanophenoxy)pyrimidin-4-yloxy)phenyl]-3-methoxypropenoate as the residue (45.5% isolated yield).

EXAMPLE 33

Methyl 2-[2-(6-chloropyrimidin-4-yloxy)phenyl]-3,3-dimethoxypropanoate in methylcyclohexane/chloromethoxypyrimidine (181.7 g, 60.57 % strength) was vacuum distilled to leave the propanoate melt. A solution of the potassium salt of 2-cyanophenol was then prepared by mixing 2-cyanophenol (46.1 g), potassium carbonate (72.1 g) and polyethylene glycol 400 (69.6 g) in water (150 g). This solution was added to the melt, which had previously been cooled to 70° C. The resulting mixture was stirred at 101° C. for 16 hours under atmospheric distillation. 55.2 area % of (E)-methyl 2-[2-(6-(2-cyanophenoxy)pyrimidin4-yloxy)phenyl]-3-methoxypropenoate was produced. The solution was then allowed to distill under atmospheric pressure at 105–120° C. for a further 2 hours 30 minutes. A further portion of water (300 ml) was added to the solution. The organic layer was separated. Methanol (120 ml) was added to the melt. The resulting mixture was cooled to ambient and held overnight. The mixture was filtered to leave (E)-methyl 2-[2-(6-(2-cyanophenoxy)-pyrimidin-4-yloxy)phenyl]-3-methoxypropenoate as the residue (30.3% isolated yield).

EXAMPLE 34

Methyl 2-[2-(6-chloropyrimidin-4-yloxy)phenyl]-3,3-dimethoxypropanoate in methylcyclohexane/chloromethoxypyrimidine (52.3 g, 60.57% strength) was vacuum distilled to leave the propanoate melt. A solution of the potassium salt of 2-cyanophenol was then prepared by mixing 2-cyanophenol (13.2 g), potassium carbonate (20.7 g), N-methyl-2-pyrrolidinone (15.0 g) in water (35 g). The solution was added to the melt, which had previously been cooled to ca. 90° C. The resulting mixture was stirred at 104° C. for 14 hours 30 minutes. Any distillates were allowed to come off under atmospheric conditions. (E)-methyl 2-[2-(6-(2-cyanophenoxy)pyrimidin4-yloxy)phenyl]-3-methoxypropenoate was produced (65.7 area %). The temperature of the reaction solution was then allowed to increase gradually to 120° C. over a period of 1 hour 15 minutes. Toluene was added to the solution. The organic layer was then separated. Toluene and N-methyl-2-pyrrolidinone were removed from the organic phase (100° C., 20 mmHg). The melt was cooled to 90° C. after which methanol (40 ml ) was added to help cooling to 65–75° C. The resulting mixture was cooled to ambient and held overnight. It was then cooled to 0–5° C. and kept at this temperature for 1 hour. The mixture was filtered to leave (E)-methyl 2-[2-(6-(2-cyanophenoxy)pyrimidin-4-yloxy)phenyl]-3-methoxypropenoate as the residue (44.7% isolated yield).

What is claimed is:

1. A process for preparing (E)-methyl 2-[2-(6-(-cyanophenoxy)pyrimidin-4-yloxy)phenyl]-3-methoxypropenoate comprising contacting (E)-methyl 2-[2-(6-chloropyrimidin-4-yloxy)phenyl]-3-methoxypropenoate or methyl 2-[2-(6-chloropyrimidin-4-yloxy)phenyl]-3,3-dimethoxypropanoate with 2-cyanophenate anions in which said 2-cyanophenate anions are generated in situ by reacting 2-cyanophenol with an alkali metal carbonate, said process being conducted in the absence of copper or a copper salt and in the absence of N,N-dimethylformamide.

2. A process according to claim 1 in which the alkali metal carbonate is potassium carbonate.

3. A process according to claim 1 in which the process is conducted in the absence of any water miscible solvent other than water itself.

4. A process according to claim 1 in which the process is conducted in the absence of any solvent or mixture of solvents.

5. A process according to claim 1 in which the process is conducted using water as a solvent.

6. A process according to claim 1 in which the process is conducted in water and a water-immiscible solvent or mixture of water-immiscible solvents.

7. A process according to claim 6 in which the water immiscible solvent is a cyclic hydrocarbon.

\* \* \* \* \*